(12) United States Patent
Karbal et al.

(10) Patent No.: US 8,558,010 B2
(45) Date of Patent: Oct. 15, 2013

(54) AZIRIDINATION OF OLEFINS

(75) Inventors: Pratibha Uttam Karbal, Pune (IN); Pandurang Vilasrao Chouthaiwale, Pune (IN); Gurunath Mallappa Suryavanshi, Pune (IN); Arumugam Sudalai, Pune (IN); Tanveer Mahamadali Shaikh, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/269,020

(22) Filed: Oct. 7, 2011

(65) Prior Publication Data

US 2012/0215011 A1 Aug. 23, 2012

(30) Foreign Application Priority Data

Dec. 27, 2010 (IN) .......................... 3102/DEL/2010

(51) Int. Cl.
*C07D 203/02* (2006.01)
*C07D 203/06* (2006.01)

(52) U.S. Cl.
USPC ......................................... 548/954; 548/969

(58) Field of Classification Search
USPC ................................................ 548/954, 969
See application file for complete search history.

(56) References Cited

U.S. PATENT DOCUMENTS 5,929,252 A  7/1999  Sharpless et al. ............. 548/968

OTHER PUBLICATIONS

Dewkar et al. Org. Lett., 2003, 5, 4501-4504.*
Ali et al., "Pyridinium hydrobromide perbromide: a versatile catalyst for aziridination of olefins using Chloramine-T," *Org. Lett.*, 1(5):705-707, 1999.
Ando, "Iodine-catalyzed aziridination of alkenes using Chloramine-T as a nitrogen source," *Tetrahedron*, 54(44):13485-13494, 1998.
Breslow et al., "Intramolecular nitrene C—H insertions mediated by transition-metal complexes as nitrogen analogs of cytochrome P-450 reactions," *J. Am. Chem. Soc.*, 105(22):6728-6729, 1983.
Campbell et al., "The action of grignard reagents on oximes. III. The mechanism of the action of arylmagnesium halides on mixed ketoximes. A new synthesis of ethyleneimines," *J. Org. Chem.*, 8(1):103-109, 1943.
Cardillo et al., "Aziridines and oxazolines: Valuable intermediates in the synthesis of unusual amino acids," *Aldrichimca Acta*, 36(2):39-50, 2003.
Cui et al., "Efficient aziridination of olefins catalyzed by a unique disilver(I) compound," *J. Am. Chem. Soc.*, 125(52):16202-16203, 2003.
Gao et al., "Cobalt-catalyzed efficient aziridination of alkenes," *Organic Letters*, 7(15):3191-3193, 2005.
Hoch, "Hoch-Campbell Synthesis," *Compt. Rend.*, 198:1865-1868, 1934.
Hodgkinson and Shipman, "Chemical synthesis and mode of action of the azinomycins," *Tetrahedron*, 57:4467, 2001.
Knight et al., "Synthesis of N-p-Toluenesulphonyl-2-alkenyl aziridines by regioselective aziridination of 1,3-Dienes," *Synlett.*, (9):949-951, 1995.
Majumdar et al., "Synthesis of cyclic sulfonamides via Pd-Catalyzed intramolecular coupling reaction: an expedient approach to polycyclic sultams," *Synlett.*, (18): 2851-2855, 2008.
McCoull and Davies, "Recent synthetic applications of chiral aziridines," *Synthesis*, (10):1347-1365, 2000.
Osborn and Sweeney, "The asymmetric synthesis of aziridines," *Tetrahedron: Asymmetry*, 8(11):1693-1715, 1997.
Padwa and Woodhouse In: *Comprehensive Heterocyclic Chemistry*, W. Lwowski, Ed., Pergamon: Oxford, vol. 7, 47-93, 1984.
Shen et al., "Unexpected multiple electrophilic addition reaction of (Z)-alk-2-en-4-ynoates with N,N-dibromo-p-toluenesulfonamide (TsNBr(2)): a highly diastereoselective synthesis of densely functionalized aziridines," *Organic Letters*, 11(24):5698-5701, 2009.
Sweeney, "Aziridines: epoxides' ugly cousins?," *Chem. Soc. Rev.*, 31(5):247-258, 2002.
Tanner, "Chiral Aziridines—their synthesis and use in stereoselective transformations ," *Angew Chem. Int. Ed. Engl.*, 33:599-619, 1994.
Wenker, "The preparation of ethylene imine from monoethanolamine," *J. Am. Chem. Soc.*, 57(11):2328-2328, 1935.

\* cited by examiner

*Primary Examiner* — Jason M Nolan
(74) *Attorney, Agent, or Firm* — Fulbright & Jaworski LLP

(57) ABSTRACT

A process for aziridination of olefins using NaIO4/alkali metal bromide/H+/Chloramine-T combination in presence of dipolar aprotic solvent under ambient conditions to obtain aziridines is disclosed.

10 Claims, 1 Drawing Sheet

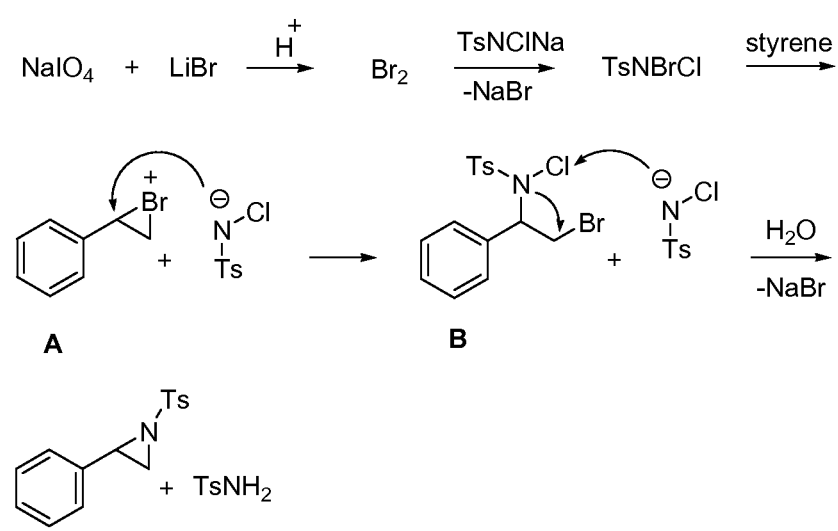

AZIRIDINATION OF OLEFINS

FIELD OF THE INVENTION

The present invention relates to a process for aziridination of olefins. More particularly the present invention provides milder, efficient and convenient method for the synthesis of aziridines from olefins. The present invention in particular, relates to process of aziridination of olefins mediated using NaIO4/LiBr/H+/Chloramine-T combination.

BACKGROUND OF INVENTION

Aziridines with a strained ring are of paramount importance in organic synthesis since they are valuable precursors of amino sugars, alkaloids, substituted α-amino acids or present in natural products such as mitomycins [Padwa, A.; Woolhouse, A. D. In *Comprehensive Heterocyclic Chemistry*; Lwowski, W.; Ed.; Pergamon: Oxford, 1984; Vol. 7, pp 47] and azinomycins [Hodgkinson, T. J.; Shipman, M. *Tetrahedron*, 2001, 57, 4467] that exhibit potent biological activity.

Aziridination of olefins are among the most useful transformations in organic synthesis [J. B. Sweeney, Chem. Soc. Rev. 2002, 31, 247; W. McCoull, F. A. Davies, Synthesis 2000, 1347] since aziridines constitute a key structural feature of several classes of natural products and are extremely versatile building blocks that can undergo synthetically useful transformations [W. McCoull, F. A. Davies, Synthesis 2000, 1347; A. Cardillo, L. Gentilucci, A. Tolomelli, Aldrichimica Acta 2003, 36, 39].

Aziridines can be found in natural products such as mitomycin, porfiromycin, and mitiromycin, which are potent antitumor and antibiotic agents [D. Tanner, Angew. Chem. Int. Ed. Engl. 1994, 33,599] Also, many biologically active compounds such as amino acids, β-lactam antibiotics and alkaloids have been derived from aziridines.

Classical method for the preparation of aziridine has been disclosed by Wenker and Hoch-Campbell in 1934 [H. Wenker, J. Am. Chem. Soc. 1935, 57, 2328; J. Hoch, Compt. Rend. 1934, 198, 1865; and K. N. Campbell, B. K. Campbell, J. F. McKenna, E. P. Chaput, J. Org. Chem. 1943, 8, 103]

U.S. Pat. No. 5,929,252 discloses a process for direct aziridination of olefins as well as a wide range of allylic alcohols employing phenyl trimethyl ammonium tribromide (PTAB) as a catalyst and N-iodo-N-chloro sulfonamides, chloramine salts, as the nitrogen source.

Article titled "The asymmetric synthesis of aziridines" by Helen M. I. Osborn and Joseph Sweeney in Tetrahedron: Asymmetry, Volume 8, Issue 11, 12 Jun. 1997, Pages 1693-1715 doi:10.1016/S0957-4166(97)00177-8, discloses methods for asymmetric preparation of a range of 1H-aziridines and their N-substituted analogues in presence of chiral catalysts.

Article titled "Unexpected Multiple Electrophilic Addition Reaction of (Z)-Alk-2-en-4-yn-oates with N,N-Dibromo-p-toluene sulfonmide (TsNBr$_2$): A Highly Diastereoselective Synthesis of Densely Functionalized Aziridines" by Shen, Huang, Xiang et al in ORGANIC LETTERS 11 (24): 5698-5701 DEC 17 2009; ISSN: 1523-7060; DOI: 10.1021%1902446h, discloses electrophilic addition reaction of (Z)-alk-2-en-4-ynoates and TsNBr2 to obtain aziridine derivatives.

Article titled "Pyridiniumhydrobromideperbromide: a versatile catalyst for aziridination of olefins using Chloramine-T" by Ali S I, Nikalje M D, Sudalai Org Lett. 1999 Sep. 9; 1(5): 705-7 discloses Pyridiniumhydrobromideperbromide (PyxHBr3) as a catalyst for the aziridination of electron-deficient as well as electron-rich olefins using Chloramine-T as a nitrogen source to obtain the corresponding aziridines.

Article titled "Iodine-catalyzed aziridination of alkenes using Chloramine-T as a nitrogen source" by Takeya Ando, in Tetrahedron Volume 54, Issue 44, 29 Oct. 1998, Pages 13485-13494 having doi: 10.1016/S0040-4020(98)00827-8 discloses aziridination of alkenes utilizing Chloramine-T (N-chloro-N-sodio-p-toluenesulfonamide) as a nitrogen source and in presence of a catalyst.

Several reported methods for aziridination reactions are known that employ catalysts such as Cu [Knight, J. G.; Muldowney, M. D. Synlett 1995, 949]; Co [Gao, G.-Y.; Harden, J. D.; Zhang, X. P. Org. Lett. 2005, 7, 3191]; Rh [Breslow, R.; Gellman, S. H. J. Am. Chem. Soc. 1983, 105, 6728]; Ag [Cui, Y.; He, C. J. Am. Chem. Soc. 2003, 125, 16202]; Pd [Majumdar, K. C.; Mondal, S.; De, N. Synlett, 2008, 2851], etc., which generates in situ metal-nitrene species (PhI=NTs) in presence of sulfonamide and oxidant.

However, the reagents employed in the prior art methods are complex, require large excess of olefins, are costly or involve toxic heavy metals. Also the earlier methods for the preparation of aziridine shows that the reactions are drastic on using metal catalysts, separation of metals from the final aziridines products was tedious. Hence, it is desirable to provide an inexpensive, easy and environmentally benign method of aziridination.

SUMMARY OF THE INVENTION

The main object of the present invention is to provide a process for the aziridination of olefins.

Another objective of the present invention is to provide simple, inexpensive and environmentally benign method of aziridination.

Another object of the invention is to provide a process for the aziridination which is metal-free, uses readily available anhydrous chloramine-T as a nitrogen source and is carried out under mild conditions displaying a wide range of substrate scope.

Accordingly, the present invention relates to a process for aziridination of olefins aziridination using NaIO4/LiBr/H+/Chloramine-T combination under ambient conditions. In another aspect, the present invention relates to one pot synthesis of aziridines from olefin.

Another embodiment of the present invention provides a process for aziridination of olefins which comprising the steps of:
a) mixing an olefin with anhydrous Chloramine-T as the nitrogen source and a dipolar aprotic solvent to form a reaction mixture;
b) adding NaIO4, alkali metal bromide and sulphuric acid to the reaction mixture as obtained in step (a) followed by stirring at temperature ranging between 25° C. to −40° C. for a period ranging between 8-12 hrs;
c) diluting the reaction mixture as obtained in step (b) in an organic solvent, washing with water and an organic solvent. Separating organic layer, drying, concentrating to the extent all organic solvent is removed, purifying to obtain the aziridated product.

In another embodiment of the present invention, olefin used in step (a) is selected from the group consisting of aliphatic and aromatic olefins.

In another embodiment of the present invention, aziridated product as obtained in step (c) is selected from the group consisting of aliphatic and aromatic aziridines.

In another embodiment of the present invention, the alkali metal bromide used in step (b) is selected from LiBr, NaBr, KBr.

In another embodiment of the present invention, the dipolar aprotic solvents used in step (a) is selected from acetone, diethylacetate, acetonitrile, THF, DMSO, ethyl methyl ketone, DMF, dimethyl acetamide.

In an embodiment of the present invention, aprotic solvent is acetonitirile, and organic solvent is ethyl acetate for diluting in step (c).

In another embodiment of the present invention, mol ratio of olefin:alkali metal bromide: NaIO4: Chloramine-T is in the range of 1:1:5:25 to 5:5:10:30 equivalents preferably 3:3:6: 30.

In another embodiment of the present invention, yield of aziridated product is in the range of 40-81%.

In another embodiment of the present invention, the aziridination of olefins is metal free.

BRIEF DESCRIPTION OF THE DRAWING

FIG. 1: Describes the mechanistic pathway involved in the aziridination of olefins.

DETAILED DESCRIPTION

The invention will now be described in detail in connection with certain preferred and optional embodiments, so that various aspects thereof may be more fully understood and appreciated and briefly described as follows.

In line with the objectives, the present invention discloses a milder, efficient and convenient method for the synthesis of aziridines from olefins under ambient conditions, which is metal free, in good yields.

The present inventors have observed that the use of p-toluene sulfonamide (p-TsNH2) as a source of nitrogen was not effective for aziridination reactions. The use of Chloramine-T trihydrate (TsNClNa.$_3$H$_2$O) as an oxidant though finds wide synthetic applications in aminohydroxylation and aminochalcogenation of olefins or its allylicaminationviabromonium intermediate, however, suffered from a lack of substrate scope, so also the use of metal bromides alone, molecular bromine, NBS as a bromine source.

Thus in the present invention, anhydrous Chloramine-T have been employed which can act both as an oxidant as well as the nitrogen source. The bromine source is monovalent alkali bromide such as NaBr, LiBr and KBr. The oxidation of the alkali bromide is carried out by an oxidizing agent, preferably hyper valentiodine source, more preferably NaIO4.

The present invention discloses an effective, milder and efficient one pot aziridination of olefins mediated using NaIO4/LiBr/H+/Chloramine-T combination under ambient conditions.

The solvents for the process are selected from dipolar aprotic solvents such as acetone, ethylacetate, acetonitrile, THF, DMSO, ethyl methyl ketone, DMF, dimethylacetamide, etc.

The aziridination of olefins of the present invention is generalized below:

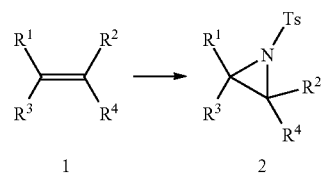

where the "R" substituents that functionalize the olefins are selected from:
(a) monosubstituted olefins: $R^1$=$R^2$=$R^4$=H, and $R^3$=straight or branched chain alkyl optionally substituted with halo or —CH2OH or —CH2OR(R=Ac, Me, Et, or cycloalkanes or aryl optionally substituted with halo, alkyl, haloalkyls, nitro, —OX(X=H, Me, Et), —NH2 or arylalkyls;
(b) disubstituted olefins: where (i) cis: $R^1$=$R^2$=H, $R^3$=straight or branched chain alkyl optionally substituted with halo or —CH2OH or —CH2OR(R=Ac, Me, Et) or cycloalkanes or aryl optionally substituted with halo, alkyl, haloalkyls, nitro, —OX(X=H, Me, Et), —NH2 or arylalkyls, $R^4$=straight or branched chain alkyl optionally substituted with halo or —CH2OH or —CH2OR(R=Ac, Me, Et,) or cycloalkanes or aryl optionally substituted with halo, alkyl, haloalkyls, nitro, —OX(X=H, Me, Et), —NH2 or arylalkyls; or (ii) trans: $R^1$=$R^4$=H, R3=straight or branched chain alkyl optionally substituted with halo or —CH$_2$OH or —CH2OR(R=Ac, Me, Et) or cycloalkanes or aryl optionally substituted with halo, alkyl, haloalkyls, nitro, —OX(X=H, Me, Et), —NH2 or arylalkyls, $R^2$=straight or branched chain alkyl optionally substituted with halo or —CH2OH or —CH2OR(R=Ac, Me, Et) or cycloalkanes or aryl optionally substituted with halo, alkyl, haloalkyls, nitro, —OX(X=H, Me, Et), —NH2 or arylalkyls;
(c) cyclic: (i) $R^1$=$R^2$=$R^4$=H, $R^3$=aryl optionally substituted with halo, alkyl, haloalkyls, nitro, —OX(X=H, Me, Et), —NH2 or arylalkyls or cycloalkanes; or (ii) where $R^1$=$R^2$=H, $R^3$ and $R^4$ from a cyclic hydrocarbon such as cyclohexene, cycloheptene, cyclooctene, or (iii) $R^1$, $R^2$, $R^3$, and $R^4$ together form a polycyclic ring such as indene, pyrene, benzopyrene, etc.;
(d) α,β unsaturated compounds: (i) $R^1$=$R^2$=H, $R^3$=H or lower alkyl or aryl, optionally substituted with lower alkyl, alkoxy, halo, haloalkyl, nitro, amino, $R^4$=COR (R=lower alkyl, phenyl), or —COOR'(R'=H, Me, Et, C3H$_7$), or —CN, or (ii) $R^1$=$R^3$=H, $R^2$=H, or lower alkyl or aryl, optionally substituted with lower alkyl, alkoxy, halo, haloalkyl, nitro, amino, or $R^4$=—CHO, COR(R=lower alkyl, phenyl), or —COOR' (R'=H, Me, Et, C3H7), or —CN.

The typical condition for the process includes 30 mol % of NaIO4, 1 equv of LiBr, 2 equv of chloramine T, 30 mol % of H$_2$SO$_4$ in acetonitrile as a solvent at 25° C. for 10-12 hours. The one pot process of the present invention comprises: admixing the olefin with Chloramine-T as the nitrogen source and a solvent to form a reaction mixture; adding NaIO4, LiBr and sulphuric acid to the above mixture, stirred at 25° C.; and diluting the reaction mixture obtained in step (b) in an organic solvent, washing with water and an organic solvent, drying, concentrating, purifying to obtain the desired aziridinated product.

The organic solvent is selected from diethyl ether, MTBE, sodium acetate, ethylacetate, brine, sat. sodiumthiosulphate, etc.

A plausible mechanistic pathway for the formation of aziridines 2 is studied using styrene (3 mmol) as the functionalized olefin and treating with NaIO4/LiBr/H+/Chloramine-T combination. The mechanism is outlined in FIG. 1. Although the exact nature of the species involved in the reaction is not known, our earlier studies had shown that 1 equiv of NaIO$_4$ was sufficient to oxidize 8 equiv of Br$^-$ ions, (IO$_4^-$+8H$^+$+8e$^-$→4H$_2$O+I$^-$). Hence, only 30 mol % of NaIO$_4$ was required to bring about 100% conversions. From the above facts and the evidence provided by the cyclic voltametry study, it is believed that Br$_2$, generated by the NaIO$_4$-mediated oxidation of LiBr in acidic condition, reacts with chloramine-T to give the reactive species TsNBrCl, which then subsequently adds onto styrene to form bromonium ion A. The stereospecific opening of A with TsNCl$^-$ at the benzylic position occurs to give β-bromo-N-chloro-N-toluenesulfonamide (B). Finally, cyclization of B with another molecule of chloramine-T results in the formation of aziridine, along with the generation of 1 mole of TsNCl$_2$; the hydrolysis of which leads to isolation of TsNH$_2$ as the byproduct.

Aromatic olefins including indene and trans-stilbene and aliphatic olefins underwent the aziridination smoothly to give corresponding aziridines in good yields. Notably, substrates like cyclohexene, cyclooctene and vinylcyclohexane gave the corresponding aziridine as sole product without allylicamination (Table 1, Entry 10). In case of α,β-unsaturated esters, the reaction was found to be however slow and gave poor yields of the expected aziridinated products (Table 2, Entry 1-6). Unsaturated aldehydes and alcohols failed to give the product.

NaIO4/LiBr mediated aziridination of olefins is summarized in Tables 1 and 2 below:

TABLE 1

| entry | substrate (1) | product$^b$ (2) | yield$^c$ (%) | m.p. (° C.) |
|---|---|---|---|---|
| 1 | Styrene (R = H) | 2a | 81 (R = H) | 92-94 |
|   | O-chlorostyrene (R= Cl) | 2b | 79 (R = Cl) | gum |
| 2 | p-Chlorostyrene | 2c | 77 (R = Cl) | 115-116 |
|   | p-Flourostyrene | 2d | 75 (R = F) | 136-138 |
|   | p-Bromostyrene | 2e | 72 (R = Br) | 127-129 |
|   | p-methylstyrene | 2f | 40 (R = CH$_3$) | 130-131 |
| 3 | 3-Phenylpropene | 2g | 80 | gum |
| 4 | p-cholomethylstyrene | 2h | 65 | 101-103 |
| 5 | t-Stilbin | 2i | 64 | 140-142 |

TABLE 1-continued

| entry | substrate (1) | product[b] (2) | yield[c] (%) | m.p. (° C.) |
|---|---|---|---|---|
| 6 |  n-Octene | 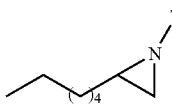 2j | 60 | gum |
| 7 | 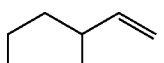 1-cyclohexaneethelene | 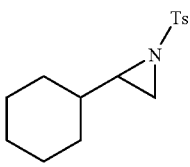 [SMILES: Cc1ccc(S(=O)(=O)N2CC2C2CCCCC2)cc1] 2k | 58 | 94-95 |
| 8 | 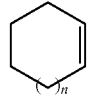 cyclohexne cyclooctene | 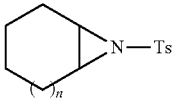 2l 2m | 60 (n = 1) 48 (n = 3) | 55-57 122-123 |
| 9 | 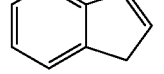 Indene | 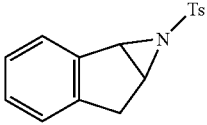 [SMILES: Cc1ccc(S(=O)(=O)N2C3Cc4ccccc4C32)cc1] 2n | 52 | 164-166 |
| 10 | 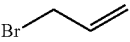 n-Bromopropene | 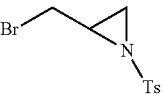 2o | 60 | 75-78 |

Reaction conditions:
[a]alkenes (3 mmol), LiBr (3 mmol), chloramine-T (6 mmol), NaIO$_4$ (30 mol %), H$_2$SO$_4$ (30 mol %), 25 ° C., 12 h;
[b]products were characterized by m.p., IR, $^1$H and $^{13}$C NMR and elemental analysis;
[c]Isolated yield after chromatographic purification;
[d]30% of aminobrominated product was formed.

TABLE 2

| Entry | Substrate 1 | Product[b] 2 | Yield (%)[c] |
|---|---|---|---|
| 1 |  Ethylcinnamate | 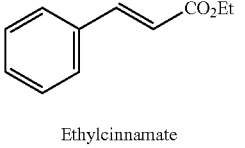 | 18 |
| 2 | 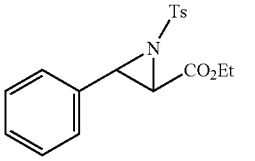 [SMILES: CCOC(=O)C1C(c2ccccc2)N1S(=O)(=O)c1ccc(C)cc1] Methylcinnamate | 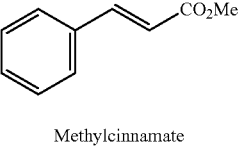 | 17 |

TABLE 2-continued

| Entry | Substrate 1 | Product[b] 2 | Yield (%)[c] |
|---|---|---|---|
| 3 | p-nitrocinnamate (O$_2$N-C$_6$H$_4$-CH=CH-CO$_2$Et) | N-Ts aziridine with p-O$_2$N-C$_6$H$_4$ and CO$_2$Et | 10 |
| 4 | p-Fluorocinnamate (F-C$_6$H$_4$-CH=CH-CO$_2$Et) | N-Ts aziridine with p-F-C$_6$H$_4$ and CO$_2$Et | 15 |
| 5 | p-Cluorocinnamate (Cl-C$_6$H$_4$-CH=CH-CO$_2$Et) | N-Ts aziridine with p-Cl-C$_6$H$_4$ and CO$_2$Et | 15 |
| 6 | p-Methoxycinnamate (MeO-C$_6$H$_4$-CH=CH-CO$_2$Et) | N-Ts aziridine with p-MeO-C$_6$H$_4$ and CO$_2$Et | 5 |

Reaction conditions:
[a] alkenes (3 mmol), LiBr (3 mmol), chloramine-T (6 mmol) NaIO$_4$ (30 mol %), H$_2$SO$_4$ (30 mol %), 25 °C., 12 h;

EXAMPLES

The present invention is illustrated herein below with examples, which are illustrative only and should not be construed to limit the scope of the present invention in any manner.

General Procedure for Aziridination of Olefins:

To a stirred solution of olefin (3 mmol) in dry CH$_3$CN (25 mL), anhydrous chloramine-T (1.365 g, 6 mmol), LiBr (0.257 g, 3 mmol), NaIO$_4$ (0.192 g 30 mol %), and conc. H$_2$SO$_4$ (0.088 g, 30 mol %) were added at 25° C. The resulting reaction mixture was stirred at 25° C. (monitored by TLC). After completion, the reaction mixture was diluted with EtOAc (15 mL) and washed with water followed by aq. saturated Na$_2$S$_2$O$_3$ (2×15 mL) solution. The organic layer was dried over anhyd. Na$_2$SO$_4$, concentrated under pressure to afford crude product, which was purified by column chromatography on silica gel using pet. ether and EtOAc (10:1) as eluent to afford pure aziridines 2a-o.

Examples: 1

N-(p-Toluenesulfonyl)-2-phenylaziridine (2a)

Yield: 81%; mp: 92-94° C.; IR (CHCl$_3$, cm$^{-1}$): 911, 1020, 1160, 1187, 1219 1324, 1399, 1455, 1528, 1696, 2926, 2956, 3025, 3130, 3321, 3933; $^1$H NMR (200 MHz, CDCl$_3$) δ 2.40 (d, J=4.6 Hz, 1H), 2.45 (s, 3H), 3.00 (d, J=7.3 and 4.6 Hz, 1H), 7.15-7.45 (m, 7H), 7.90 (d, J=8.26 Hz, 2H); $^{13}$C NMR (50 MHz, CDCl$_3$): 23.27, 36.51, 41.55, 126.59, 127.15, 128.58, 129.15, 129.23, 130.31, 135.70, 135.83, 145.05; Anal. Calcd for C$_{16}$H$_{17}$NO$_2$S requires C, 65.91; H, 5.93; N, 5.10%. found C, 65.80; H, 6.01; N, 4.90%.

Examples: 2

N-(p-Toluenesulfonyl)-2-benzylaziridine (2g)

Yield: 80%; gum; IR (CHCl$_3$, cm$^{-1}$): 675, 770, 840, 915, 1090, 1130, 1250, 1355, 1370, 1400, 1480, 2880, 2910, 2980, 3280; $^1$H NMR (200 MHz, CDCl$_3$) δ 2.14 (d, J=4.5 Hz, 1H), 2.43 (s, 3H), 2.65-2.78 (m, 3H), 2.82-2.93 (m, 1H), 7.01-7.07 (m, 2H), 7.12-7.26 (m, 5H), 7.68 (d, J=8.4 Hz, 2H); $^{13}$C NMR (50 MHz, CDCl$_3$): 21.4, 32.5, 37.2, 40.9, 126.2, 127.7, 128.2, 128.5, 129.3, 134.4, 136.8, 143.9; Anal. Calcd for C$_{16}$H$_{17}$NO$_2$S requires C, 66.87; H, 5.96; N, 4.87%. found C, 66.80; H, 6.01; N, 4.90%.

Examples: 3 trans-N-(p-Toluenesulfonyl)-2-3-diphenylaziridine (2i)

Yield: 64%; 140-142; IR (CHCl$_3$, cm$^{-1}$): 980, 1020, 1180, 1240, 1380, 1450, 2653, 2800, 3000, 3280; $^1$H NMR (200 MHz, CDCl$_3$) δ, 2.40 (s, 3H), 4.25 (s, 2H), 7.05-7.70 (m, 12H), 7.85 (d, J=8.26 Hz, 2H); $^{13}$C NMR (50 MHz, CDCl$_3$): 21.64, 35.94, 40.49, 45.55, 126.34, 126.87, 127.94, 128.78, 129.70, 135.39, 137.54, 144.51; Anal. Calcd for C$_{16}$H$_{17}$NO$_2$S requires C, 72.18; H, 5.47; N, 4.00%. found C, 72.20; H, 5.41; N, 3.98%.

Examples: 4

7-[Methyl-7-(phenyl sulfonyl)-7-azabicyclo[4.1.0]heptane (2l)

Yield: 60%; 55-57; IR(CHCl$_3$, cm$^{-1}$): 920, 964, 1090, 1156, 1184, 1238, 1320, 1400, 1480, 1439, 1597, 2862, 3937; $^1$H NMR (200 MHz, CDCl$_3$) δ 1.05-1.45 (m, 4H), 1.65-1.80 (m, 4H), 2.45 (s, 3H), 2.65-2.78 (m, 3H), 2.95 (t, J=1.3 Hz, 2H), 7.35 (d, J=8.26 2H), 7.85 (d, J=8.26 Hz, 2H); $^{13}$C NMR (50 MHz, CDCl$_3$): 19.41, 21.57, 22.76, 24.06, 39.58, 127.59, 129.50, 136.03, 143.79; Anal. Calcd for C$_{16}$H$_{17}$NO$_2$S requires C, 62.12; H, 6.81; N, 5.52%. found C, 62.08; H, 6.81; N, 5.52%.

Examples: 5

9-[Methyl-7-(phenyl sulfonyl)-7-azabicyclo[4.1.0]heptane (2m)

Yield: 48%; 122-123; IR (CHCl$_3$, cm$^{-1}$): 964, 1090, 1159, 1184, 1237, 1320, 1403, 1442, 1597, 2860, 2940; $^1$H NMR (200 MHz, CDCl$_3$) δ1.30-1.170 (m, 10H), 2.05 (m, 2H), 2.45 (m, 3H), 2.80 (m, 2H), 7.35 (d, J=8.26, 2H), 7.85 (d, J=8.26 Hz, 2H); $^{13}$C NMR (50 MHz, CDCl$_3$): 22.13, 25.16, 26.72, 26.94, 128.13, 136.08, 136.59 144.39; Anal. Calcd for C$_{16}$H$_{17}$NO$_2$S requires C, 64.48; H, 7.56; N, 5.01%. found C, 64.52; H, 7.59; N, 4.90%.

N-(p-Toluenesulfonyl)-indeneaziridine (2n)

Examples: 6

Yield: 52%; gum; IR (CHCl$_3$, cm$^{-1}$): 675, 750, 770, 840, 915, 1090, 1130, 1158, 1250, 1323, 1370, 1400, 1480, 2880, 2980, 3280; $^1$H NMR (200 MHz, CDCl$_3$) δ 2.40 (d, J=6.48 Hz, 1H), 2.45 (s, 3H), 3.15-3.35 (dd, J=8.1, and 7.0 Hz, 1H), 3.60 (dd, J=8.1 and 7.02 Hz, 1H), 4.2-4.40 (m, 1H) 7.15-7.50 (m, 6H), 7.85 (d, J=8.26 Hz, 2H); $^{13}$C NMR (50 MHz, CDCl$_3$): 22.26, 41.71, 52.31, 67.73, 125.30, 125.39, 128.05, 128.46, 129.86, 130.41, 138.02, 139.98140.80, 144.37; Anal. Calcd for C$_{16}$H$_{17}$NO$_2$S requires C, 66.34; H, 5.29; N, 4.90%. found C, 67.0; H, 5.27; N, 4.90%.

Examples: 7

N-(p-Toluenesulfonyl)-2-bromomethylaziridine (2o)

Yield: 60%; mp: 75-78° C.; IR (CHCl$_3$, cm$^{-1}$): 1093, 1119, 1292, 1328, 1403, 1597, 2926, 2981, 3029, 3132, 3150, 3175, 3200, 3277; $^1$H NMR (200 MHz, CDCl$_3$) δ 2.45 (s, 3H), 3.50-3.65 (m, 1H), 3.75-3.80 (m 1H), 4.10-4.30 (m, 1H), 5.01-5.25 (m, 1H), 7.35 (d, J=8.2 Hz, 2H), 7.85 (d, J=8.2 Hz, 2H); $^{13}$C NMR (50 MHz, CDCl$_3$): δ 21.3, 32.8, 47.2, 49.92, 126.9 129.7, 136.6, 143.7; Anal. Calcd for C$_{10}$H$_{12}$BrNO$_2$S requires C, 41.39; H, 4.17; N, 4.83%. found C, 41.35; H, 4.19; N, 4.80%.

The invention claimed is:

1. A process for aziridination of olefins, wherein the process comprises:
   (a) mixing an olefin with chloramine-T and a dipolar aprotic solvent to form a reaction mixture;
   (b) adding NaIO$_4$, alkali metal bromide, and sulphuric acid to the reaction mixture; and
   (c) diluting the reaction mixture an organic solvent, washing with water and an organic solvent, drying, concentrating, and purifying to obtain the desired aziridated product.

2. The process of claim 1, wherein, after adding NaIO$_4$, alkali metal bromide, and sulphuric acid, the reaction mixture is stirred at a temperature ranging between 25° C. to 40° C. for a period ranging between 8-12 hrs.

3. The process of claim 1, wherein olefin is an aliphatic or aromatic olefin.

4. The process of claim 1, wherein the aziridated product is an aliphatic or aromatic aziridine.

5. The process of claim 1, wherein the alkali metal bromide used in step (b) is LiBr, NaBr, or KBr.

6. The process of claim 1, wherein the dipolar aprotic solvent comprises acetone, diethylacetate, acetonitrile, THF, DMSO, ethyl methyl ketone, DMF, or dimethyl acetamide.

7. The process of claim 1, wherein the reaction mixture has a mol ratio of olefin:alkali metal bromide:NaIO4:Chloramine-T in the range of 1:1:5:25 to 5:5:10:30 equivalents.

8. The process of claim 1, resulting in a yield of aziridated product in the range of 40-81%.

9. The process of claim 1, wherein aziridination of olefins is metal free.

10. The process of claim 1, wherein the solvent in step (c) used for diluting the reaction mixture is ethylacetate.

* * * * *